(12) United States Patent
Naddaka et al.

(10) Patent No.: US 7,323,568 B2
(45) Date of Patent: *Jan. 29, 2008

(54) PROCESS FOR PREPARING IMIQUIMOD

(75) Inventors: Vladimir Naddaka, Lod (IL); Shady Saeed, Haifa (IL); Dionne Montviliski, Givataim (IL); Lior Zelikovitch, Mazkeret Batia (IL); Oded Arad, Rechovot (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/298,711

(22) Filed: Dec. 12, 2005

(65) Prior Publication Data

US 2007/0135640 A1   Jun. 14, 2007

(51) Int. Cl.
*C07D 471/00* (2006.01)
(52) U.S. Cl. ...................................... 546/82
(58) Field of Classification Search .................. 546/82
See application file for complete search history.

(56) References Cited

U.S. PATENT DOCUMENTS

| | | | |
|---|---|---|---|
| 4,689,338 A * | 8/1987 | Gerster | 514/293 |
| 4,929,624 A | 5/1990 | Gerster et al. | |
| 4,988,815 A | 1/1991 | André et al. | |
| 5,175,296 A | 12/1992 | Gerster | |
| 5,367,076 A | 11/1994 | Gerster | |
| 2005/0085500 A1 | 4/2005 | Gutman et al. | |

OTHER PUBLICATIONS

Rondestvedt, Journal of Organic Chemistry, 1977, 42(19), 3118.*
Rondestvedt Jr. "Aminations With Ammonia and Formamide, Synthesis of Terephtalamic Acid and of P-Nitroaniline", Journal of Organical Chemistry, 42(19): 3118-3123, 1977.
Pachter et al. "Methylation of Some Amides in Acetone", Journal of the American Chemical Society, 74: 1321-1322, 1952.
Bredereck et al. "Umsetzungen von Halogenverbindungen mit Formamid (Formamid-Reaktionen, III. Mitteilung)", Chemische Berichte, 87(4): 537-546, 1954. English Abstract.

* cited by examiner

*Primary Examiner*—D. Margaret Seaman
*Assistant Examiner*—Nizal S. Chandrakumar

(57) ABSTRACT

The present invention provides a process for preparing 4-amino-1-isobutyl-1H-imidazo[4,5-c]quinoline (Imiquimod) of formula (I).

The process comprises heating 4-chloro-1-isobutyl-1H-imidazo[4,5-c]quinoline of formula (II) with formamide, and optionally with bubbling of gaseous ammonia to afford Imiquimod of formula (I).

According to the present invention, by using this process and novel purification methods, essentially as described herein, highly pure Imiquimod is obtained.

23 Claims, No Drawings

PROCESS FOR PREPARING IMIQUIMOD

FIELD OF THE INVENTION

The present invention provides a process for converting the starting material 4-chloro-1-isobutyl-1H-imidazo[4,5-c] quinoline to highly pure Imiquimod by reacting it with formamide and optionally in the presence of ammonia.

BACKGROUND OF THE INVENTION 4-amino-1-isobutyl-1H-imidazo[4,5-c]quinoline, also known as Imiquimod, is an immune response modifier, useful for treating genital warts. The drug is marketed as a 5% cream under the trade name Aldara® and has the following structural formula (I):

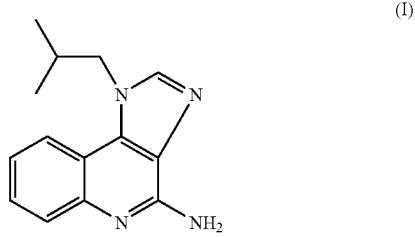

(I)

The synthesis of Imiquimod was described in several patents, for example in U.S. Pat. Nos. 4,689,338 and 4,929,624 (to Minnesota Mining and Manufacturing Co. Inc.). The final step of the processes described therein involves an ammonolysis reaction carried out by heating the compound 4-chloro-1-isobutyl-1H-imidazo[4,5-c]quinoline of formula (II) in the presence of ammonium hydroxide or ammonia in methanol under high pressure (e.g. in a steel bomb) at 150° C. to afford Imiquimod of formula (I), as depicted in Scheme 1.

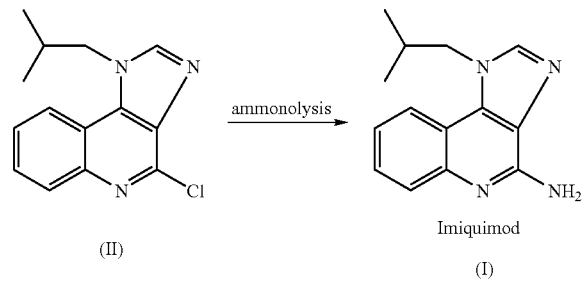

Scheme 1

(II) ammonolysis → Imiquimod (I)

U.S. Pat. No. 4,988,815 describes a different process for preparing Imiquimod, however the said final step also involves the same ammonolysis of the compound 4-chloro-1-isobutyl-1H-imidazo[4,5-c]quinoline.

Another process is disclosed in U.S. Pat. No. 5,175,296, wherein the compound 1H-imidazo[4,5-c]quinoline 5N-oxide is reacted with benzoyl isocyanate and the product is hydrolyzed to obtain Imiquimod.

U.S. Pat. No. 5,367,076 discloses another process of preparing Imiquimod, wherein the compound 1H-imidazo [4,5-c]quinoline 5N-oxide is reacted with an acylating agent and the product is aminated to obtain Imiquimod.

US Patent Application Publication No. 2005/0085500 discloses yet another process for preparing Imiquimod, wherein the compound 4-chloro-1-isobutyl-1H-imidazo[4,5-c]quinoline is converted to Imiquimod in three steps. In the first step the compound 4-(N-benzylamino)-1-isobutyl-1H-imidazo[4,5-c]quinoline is obtained by reacting 4-chloro-1-isobutyl-1H-imidazo[4,5-c]quinoline with benzylamine. In the second step the acid addition salt of 4-(N-benzylamino)-1-isobutyl-1H-imidazo[4,5-c]quinoline is prepared, and in the third step Imiquimod is obtained from the said acid addition salt by reaction with NaOH.

The disadvantage of the above process is that it is lengthy. The processes using ammonolysis like U.S. Pat. Nos. 4,689, 338 and 4,929,624, are also disadvantageous because the reaction is conducted at high temperature and under pressure, which is undesirable with respect to industrial safety measures.

Using benzoyl isocyanate, as taught in U.S. Pat. No. 5,175,296, is also disadvantageous because the compound is toxic and may react with water or acid to produce very toxic hydrogen cyanide gas, hence its usage in industrial processes is limited.

Thus, there is still a need in the art for an improved one-step process of preparing highly pure Imiquimod starting from 4-chloro-1-isobutyl-1H-imidazo[4,5-c]quinoline. The process should be more suitable for industrial use in comparison to the present processes for preparing Imiquimod and should enable preparing highly pure Imiquimod in a shorter synthetic preparation and more industrially feasible conditions, for example by using lower reaction temperature and/or by converting the compound of formula (II) to Imiquimod without application of high pressure.

Ammonolysis in relatively milder conditions is documented in the literature. However, in the examples found, the reaction conditions are not optimal. Thus for example in "Organic Syntheses: Collective Volume 2", Ed. by A. H. Blatt, 1943, 2,4-dinitroaniline is prepared by reacting 2,4-dinitrochlorobenzene with ammonia in the presence of ammonium acetate at 170° C. without application of pressure. An alternative example is reported by Kym in Ber. 1899, 32, 3539 for preparing 2,4-dinitroaniline by hydrolysis of the 2,4-dinitroacetanilide obtained when 2,4-dinitrochlorobenzene and acetamide are heated at 200-210° C. Another option is using the example reported by Bredereck et al. in Chem. Ber. 1954, 87, 537, wherein 2,4-dinitroaniline is obtained by heating under reflux (210° C.) a solution of 2,4-dinitrochlorobenzene in formamide. Ammonolysis of chloronitrobenzenes with ammonia in formamide was carried out at high temperature without application of pressure by Rondestvedt as reported in J. Org. Chem. 1977, 42 (19), 3118 and by Niclas et al. as reported in Zeits. fuer Chem. 1985, 24(4), 137.

BRIEF SUMMARY OF THE INVENTION

The present invention provides a process for preparing 4-amino-1-isobutyl-1H-imidazo[4,5-c]quinoline (Imiquimod) of formula (I), the process comprising:

heating 4-chloro-1-isobutyl-1H-imidazo[4,5-c]-quinoline of formula (II) with formamide and optionally with ammonia bubbling to afford the compound of formula (I);

isolating the compound of formula (I); and optionally purifying the obtained compound of formula (I).

In addition, the present invention provides a crystallization method of obtaining highly pure Imiquimod having a purity of at least 98.5% and preferably having a purity equal to or greater than 99.5%, thus avoiding the use of column chromatography.

DETAILED DESCRIPTION OF THE PREFERRED EMBODIMENTS

The present invention provides a process for preparing 4-amino-1-isobutyl-1H-imidazo[4,5-c]quinoline (Imiquimod) of formula (I), the process comprising:

heating 4-chloro-1-isobutyl-1H-imidazo[4,5-c]-quinoline of formula (II) with formamide and optionally with ammonia bubbling to afford the compound of formula (I);

isolating the compound of formula (I); and optionally purifying the obtained compound of formula (I).

According to a preferred embodiment of the present invention, the reaction is carried out with formamide and in the absence of an additional solvent.

Preferably, more than 5 equivalents of formamide relative to one equivalent of the compound of formula (II) are used in the process. More preferably, 12-20 equivalents of formamide relative to one equivalent of the compound of formula (II) are used in the process.

According to another preferred embodiment of the present invention, the process is carried out at a temperature range of 135-145° C. The inventors of the present invention have discovered that by carrying out the reaction at relatively lower temperatures and longer reaction times than the literature examples, the reaction yield is improved, as suggested by the comparative table 1 (of examples 2-4).

According to one embodiment of the present invention, the process is carried out under inert atmosphere, preferably under nitrogen owing to the moisture sensitivity of the reaction mixture.

Without wishing to be bound by any particular theory it is assumed that the process involves the in situ formation of a N-formyl intermediate (III), without its isolation, followed by hydrolysis of the thus formed N-formyl intermediate to provide the compound of formula (I). The term "hydrolysis" as used herein designates not only to nucleophilic displacement with water but also to displacement with other nucleophilic compounds. Such a reaction can be carried out by general methods well known to those skilled in the art, e.g., by heating in the presence of a nucleophilic solvent such as water or a lower alkanol, optionally in the presence of a catalyst such as an alkali metal hydroxide or lower alkoxide.

Thus, according to the present invention, the N-formyl derivative is hydrolyzed in situ, without isolation, to provide the compound of formula (I). However, in case that basic hydrolysis is not applied, the N-formyl derivative can be isolated from the reaction mixture while reacting compound (II) with formamide without adding ammonia.

Formamide when heated with a halogen-containing compound at about 150° C. affords the products of N-alkylation and O-alkylation, as reported by Bredereck in Ber. 1954, 87, 537. Therefore, after reaction completion the reaction mixture may contain about 40% of 4-hydroxy-1-isobutyl-1H-imidazo[4,5-c]quinoline of formula (IV) as a by-product. The amount of the product of the O-alkylation is significantly decreased in a reaction of amides with a halogen-containing compound when this reaction is carried out in the presence of a base, as described for example by Pachter et al. in J. Am. Chem. Soc. 1952, 74, 1321.

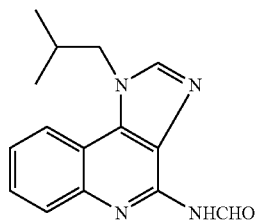

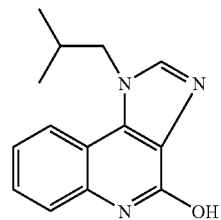

Since the progress of the reaction can be monitored by using high performance liquid chromatography (HPLC), the reaction may be stopped after complete disappearance of the starting material.

According to the present invention, after reaction completion water is added and the mixture is stirred at elevated temperature and then a mixture of water and a water-soluble base is added and stirring is maintained at ambient temperature to produce a solid, which is collected by filtration, washed and dried, optionally at elevated temperature and under reduced pressure to yield the crude Imiquimod (I).

According to another embodiment of the present invention, the said water-soluble base is a metal hydroxide selected from the group consisting of lithium hydroxide, sodium hydroxide, potassium hydroxide, and the like. Preferably the base is sodium hydroxide.

According to another preferred embodiment of the present invention, the process for preparing the compound of formula (I) may be also carried out with formamide and with gaseous ammonia bubbling. The process is carried out by heating a mixture of the compound of formula (II) and formamide with gaseous ammonia bubbling, which may be continuously bubbled into the reaction mixture, that is during the whole course of the reaction, or in installments, that is during every 15 minutes of each hour.

In accordance with the present invention, upon reaction completion only about 10-15% of the compound of formula (IV) is present in the reaction mixture.

According to another preferred embodiment of the present invention, the process is carried out with formamide and in the absence of an additional solvent Preferably, more than 5 equivalents of formamide relative to one equivalent of the compound of formula (II) are used in the process. More preferably, 12-20 equivalents of formamide relative to one equivalent of the compound of formula (II) are used in the process.

According to another embodiment of the present invention, the reaction is preferably carried out at a temperature range of 140-145° C.

According to yet another embodiment of the present invention more than 2 equivalents of ammonia relative to one equivalent of the compound of formula (II) are used in the process.

Since the progress of the reaction can be monitored by using high performance liquid chromatography (HPLC), the reaction may be ceased after complete disappearance of the starting material.

According to the present invention, after reaction completion the reaction mixture is cooled to ambient temperature and stirred at this temperature for about 3 hours. A solid is collected by filtration, washed and dried, optionally at elevated temperature and under reduced pressure to yield the crude Imiquimod (I).

In accordance with the present invention, the compound of formula (I) can be isolated from the reaction mixture by any conventional method known in the art selected, without limitation, from the group consisting of precipitation, crystallization, slurrying, washing in a suitable solvent, filtration through a packed-bed column, dissolution in an appropriate solvent (e.g., N,N-dimethylformamide) and re-precipitation by addition of a second solvent in which the compound is insoluble, and any combination of methods thereof.

According to another preferred embodiment of the present invention, the isolation and purification of the crude compound of formula (I) can be optionally carried out by adding water and a base, which may be an aqueous metal hydroxide solution to the reaction mixture thus precipitating a solid, which is collected by filtration and slurried under reflux in a mixture of an organic solvent and a base, which may be an aqueous metal hydroxide, optionally followed by consequent washings with the organic solvent, water and again with the organic solvent. Using the purification method by the said slurrying procedure, as described herein, enables obtaining a highly pure compound of formula (I) (Imiquimod) having a purity of at least 98.5%, preferably having a purity equal to or greater than 99.5%, without using column chromatography.

According to another embodiment of the present invention, the organic solvent used in the slurrying procedure is selected from the group consisting of methanol, ethanol, 1-propanol, 2-propanol, and mixtures thereof. The presently preferred organic solvent used in the slurrying procedure is methanol.

The base, which may be an aqueous metal hydroxide solution, used in the mixture with the organic solvent in the slurying procedure, is selected from the group consisting of lithium hydroxide, sodium hydroxide, potassium hydroxide, and the like. Preferably, the base is sodium hydroxide.

According to another preferred embodiment of the present invention, the purification of the crude compound of formula (I) can be optionally carried out by washing it in a suitable solvent, selected from the group consisting of water, methanol, ethanol, 1-propanol, 2-propanol, and mixtures thereof.

According to another preferred embodiment of the present invention, a method of crystallizing the compound of formula (I) (Imiquimod) is provided, the method comprising:

dissolving Imiquimod in an organic solvent, optionally at elevated temperature;
optionally filtering the hot solution;
cooling to about 20° C. and stirring; and
collecting the crystals by filtration, washing with an organic solvent and drying.

According to another embodiment of the present invention the crystallization solvent is selected from the group consisting of N,N-dimethylformamide (DMF), N,N-dimethyl acetamide (DMA), dimethyl sulfoxide (DMSO), N-methyl-2-pyrrolidone (NMP), and mixtures thereof.

According to yet another embodiment of the present invention the organic solvent used for washing the crystals is selected from the group consisting of methanol, ethanol, 1-propanol, 2-propanol, and mixtures thereof, preferably methanol.

The crystallized Imiquimod from the appropriate solvent as described herein provides highly pure product having a purity of at least 98.5%, preferably having a purity equal to or greater than 99.5%.

EXAMPLES

Example 1

Preparation of Imiguimod (I) by Reacting Compound (II) with Formamide

A mixture of 4-chloro-1-isobutyl-1H-imidazo[4,5-c]-quinoline (50.0 g, 0.192 mol) and formamide (125 ml, 3.136 mole, 16.3 equiv.) was heated at about 140° C. under nitrogen atmosphere for 26 hours. Then, the reaction mixture was cooled to 95° C. and water (10 ml) was added. The reaction mixture was heated at this temperature for 2 hours. Water (250 ml) and 47% aqueous sodium hydroxide solution were then added to produce a pH of about 9 and the mixture was stirred at ambient temperature for 2 hours. A solid was collected by filtration, washed with water (3×50 ml) and methanol (3×50 ml) and dried at 50° C. under reduced pressure overnight to give crude 4-amino-1-isobutyl-1H-imidazo[4,5-c]quinoline (Imiquimod) (39.0 g). The crude compound (39.0 g) was slurried in a mixture of methanol (500 ml) and 47% aqueous sodium hydroxide solution (about 33.0 ml) under reflux for 6 hours. The mixture was cooled to ambient temperature and a colorless solid was collected by filtration, washed with methanol (3×20 ml), water (3×20 ml) and methanol (3×20 ml) and dried at 50° C. under reduced pressure overnight to yield 22.0 g of Imiquimod in 47.6% yield, having a purity of 98.2% (by HPLC). The product was crystallized from N,N-dimethylformamide to afford colorless Imiquimod having a purity of 99.9% (by HPLC).

Examples 2-4

The data obtained by reacting the compound of formula (II) with formamide at different reaction temperatures for different reaction times is summarized in Table 1.

TABLE 1

| Example | Reaction temperature, ° C. | Reaction time, hours | Yield % |
| --- | --- | --- | --- |
| 2 | 150 | 18 | 46 |
| 3 | 160 | 7 | 40 |
| 4 | 170 | 4 | 35.7 |

Example 5

Preparing Imiquimod (I) by Reacting Compound (II) with Formamide in the Presence of Ammonia (Bubbling During the Whole Course of the Reaction)

A mixture of 4-chloro-1-isobutyl-1H-imidazo[4,5-c]quinoline (100.0 g, 0.385 mole) and formamide (250 ml, 6.27 mole, 16.3 equiv.) was heated to 145° C. under nitrogen atmosphere. Then, ammonia (gas) (92 g, 5.29 mole, 14 equiv.) was bubbled (4-5 g per hour) into the reaction mixture at this temperature during a period of 20 hours. Then, the reaction mixture was cooled to ambient temperature and stirred at this temperature for 3 hours. A colorless solid was collected by filtration, washed with methanol (3×100 ml), water (3×100 ml) and again with methanol (3×50 ml) and dried at 50° C. under reduced pressure overnight to give a crude Imiquimod (74.1 g, 80.2% yield, purity by HPLC: 99.3%). The crude compound (74.1 g) was slurried in a boiling mixture of methanol (500 ml) and 47% aqueous sodium hydroxide solution (about 6 ml) for 4 hours. The hot mixture was filtered and the thus obtained cake was washed with methanol (3×40 ml), water (3×50 ml) and again with methanol (3×40 ml) and dried at 50° C. under reduced pressure to yield 72.2 g of Imiquimod in 77.9% yield, having a purity of 99.85% (by HPLC)

Example 6

Preparation of Imiguimod (I) by Reacting the Compound of Formula (II) with Formamide in the Presence of Ammonia (Bubbling During 15 Minutes of Each Hour)

A mixture of 4-chloro-1-isobutyl-1H-imidazo[4,5-c] quinoline (400.0 g, 1.54 mole) and formamide (1000 ml, 25.08 mole, 16.3 equiv.) was heated to 145° C. under nitrogen atmosphere. Then, ammonia (gas) (60 g, 3.53 mole, 2.3 equiv.) was bubbled (2-2.5 g during 15 minutes of each hour) into the reaction mixture at this temperature during 25 hours. Then, the reaction mixture was cooled to ambient temperature and stirred at this temperature for 3 hours. A colorless solid was collected by filtration, washed with methanol (3×400 ml), water (3×400 ml) and again with methanol (3×200 ml) and dried at 50° C. under reduced pressure overnight to give 288.3 g, of crude Imiquimod in 78.0% yield, having a purity of 99.6% (by HPLC).

Example 7

Crystallization of Crude Imiguimod from Dimethyl Sulfoxide

Crude Imiquimod (288.3 g) was dissolved in dimethyl sulfoxide (5700 ml) at 140° C. and the hot solution was filtered. The filtrate was cooled to about 20° C. and the suspension was stirred at this temperature for 5 hours. The colorless crystals were collected by filtration, washed with methanol (3×400 ml) and dried at 50° C. under reduced pressure overnight to yield 279.8 g of Imiquimod in 75.5% yield, having a purity of 99.91% (by HPLC).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for preparing 4-amino-1-isobutyl-1H-imidazo[4,5-c]quinoline (Imiquimod) of formula (I)

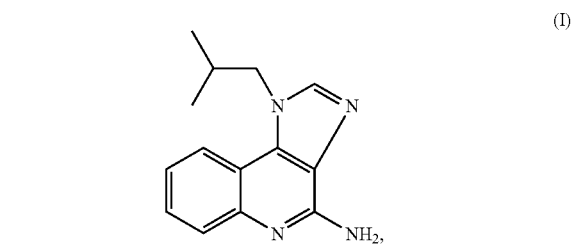

the process comprising:
heating 4-chloro-1-isobutyl-1H-imidazo[4,5-c]-quinoline of the formula (II)

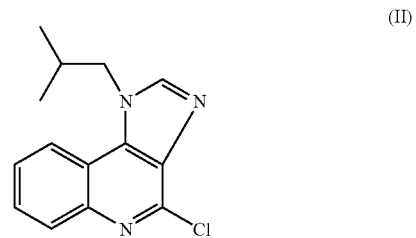

in formamide and with gaseous ammonia bubbling to afford the compound of formula (I);
isolating the compound of formula (I); and
optionally purifying the obtained compound of formula (I).

2. The process according to claim 1, wherein said heating of the compound of formula (II) with formamide is carried out at a temperature range of 135-145° C. without application of pressure.

3. The process according to claim 1, wherein said heating of the compound of formula (II) with formamide and with ammonia bubbling is carried out at a temperature range of 140-145° C.

4. The process according to claim 1, wherein gaseous ammonia is bubbled into the reaction mixture either during the whole course of the reaction or during every 15 minutes of each hour during the course of the reaction.

5. The process according to claim 4, wherein more than 2 equivalents of ammonia relative to the compound of formula (II) are used.

6. The process according to claim 1, wherein more than 5 equivalents of formamide relative to the compound of formula (II) are used.

7. The process according to claim 1, wherein the compound of formula (I) is isolated from the reaction mixture and purified by a method selected from the group consisting of precipitation, crystallization, slurrying, washing in a suitable solvent, filtration through a packed-bed column, dissolution in an appropriate solvent and re-precipitation by addition of a second solvent in which the compound is insoluble, and any combination thereof.

8. The process according to claim 7, wherein purifying the obtained compound of formula (I) comprises using a slurrying procedure under reflux in a solvent mixture, said solvent mixture comprising an organic solvent and a base.

9. The process according to claim 8, wherein said organic solvent is selected from the group consisting of methanol, ethanol, 1-propanol, 2-propanol, and mixtures thereof.

10. The process according to claim 9, wherein said organic solvent is methanol.

11. The process according to claim 8, wherein the base used in the slurrying procedure is a metal hydroxide selected from the group consisting of lithium hydroxide, sodium hydroxide, and potassium hydroxide.

12. The process according to claim 11, wherein the base is sodium hydroxide.

13. The process according to claim 7, wherein purifying the obtained compound of formula (I) comprises washing in a suitable solvent.

14. The process according to claim 13, wherein the suitable solvent for washing is selected from the group consisting of water, methanol, ethanol, 1-propanol, 2-propanol, and mixtures thereof.

15. A method of crystallizing the compound of formula (I), the method comprising:
dissolving the compound of formula (I) in an organic crystallization solvent, optionally at elevated temperature;
optionally filtering the hot solution;
cooling to about 20° C. and stirring; and
collecting the crystals by filtration, washing with an organic solvent and drying.

16. The method according to claim 15, wherein the organic crystallization solvent is selected from the group consisting of dimethyl sulfoxide (DMSO), N,N-dimethyl-formamide (DMF), N,N-dimethyl-acetamide (DMA), N-methyl-2-pyrrolidone (NMP), and mixtures thereof.

17. The method according to claim 15, wherein the organic solvent used for washing the crystals is selected from the group consisting of methanol, ethanol, 1-propanol, 2-propanol, and mixtures thereof.

18. The method according to claim 17, wherein the organic solvent used for washing the crystals is methanol.

19. The method according to claim 15, wherein the compound of formula (I) has a purity of at least 98.5%.

20. The method according to claim 15, wherein the compound of formula (I) has a purity equal to or greater than 99.5%.

21. The process according to claim 6, wherein 12-20 equivalents of formamide relative to the compound of formula (II) are used.

22. The process according to claim 7, wherein said dissolution in an appropriate solvent comprises dissolution in N,N-dimethylformamide.

23. The process according to claim 8, wherein the base comprises an aqueous solution of a metal hydroxide.

* * * * *